United States Patent
Ivkovic et al.

(10) Patent No.: US 10,849,546 B2
(45) Date of Patent: Dec. 1, 2020

(54) DIAGNOSIS OF NORMAL PRESSURE HYDROCEPHALUS BY AUTOMATED PROCESSING OF MRI IMAGES

(71) Applicant: Cornell University, Ithaca, NY (US)

(72) Inventors: Milos Ivkovic, New York, NY (US); Norman Relkin, Harrington Park, NJ (US); Henning U. Voss, New York, NY (US); Jonathan P. Dyke, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 949 days.

(21) Appl. No.: 15/035,618

(22) PCT Filed: Nov. 11, 2014

(86) PCT No.: PCT/US2014/065007
§ 371 (c)(1),
(2) Date: May 10, 2016

(87) PCT Pub. No.: WO2015/070215
PCT Pub. Date: May 14, 2015

(65) Prior Publication Data
US 2016/0270710 A1  Sep. 22, 2016

Related U.S. Application Data

(60) Provisional application No. 61/902,675, filed on Nov. 11, 2013.

(51) Int. Cl.
*A61B 5/00* (2006.01)
*G06T 7/00* (2017.01)
*A61B 5/055* (2006.01)

(52) U.S. Cl.
CPC .......... *A61B 5/4064* (2013.01); *A61B 5/0042* (2013.01); *A61B 5/055* (2013.01);
(Continued)

(58) Field of Classification Search
CPC ... A61B 5/4064; A61B 5/7282; A61B 5/0042; A61B 5/055; A61B 5/4082;
(Continued)

(56) References Cited

U.S. PATENT DOCUMENTS

| | | |
|---|---|---|
| 5,425,368 A | 6/1995 | Brandt |
| 6,163,152 A | 12/2000 | Bernstein et al. |

(Continued)

FOREIGN PATENT DOCUMENTS

EP  1 715 886 B1  2/2010

OTHER PUBLICATIONS

O'Haver, "An Introduction to Signal Processing", 2012 (accessed from https://web.archive.org/web/20120902084624/http://terpconnect.umd.edu/~toh/spectrum/TOC.html) (Year: 2012).*

(Continued)

*Primary Examiner* — Katherine L Fernandez
*Assistant Examiner* — Colin T. Sakamoto
(74) *Attorney, Agent, or Firm* — Foley & Lardner LLP

(57) ABSTRACT

Discussed herein is a parametric model for DTI MD histogram fitting, named the Generalized Voss-Dyke function, which is highly successful in segregating NPH cases from potential confounders without reliance on operator dependent region-of-interest analyses or inter-subject registration. The Generalized Voss-Dyke function is useful for managing the imaging of any tissue interfaces.

22 Claims, 11 Drawing Sheets

(52) U.S. Cl.
CPC .......... *A61B 5/4082* (2013.01); *A61B 5/4088* (2013.01); *A61B 5/7225* (2013.01); *A61B 5/7246* (2013.01); *A61B 5/7282* (2013.01); *G06T 7/0012* (2013.01); *A61B 2576/026* (2013.01); *G06T 2207/10092* (2013.01); *G06T 2207/30016* (2013.01)

(58) Field of Classification Search
CPC ... A61B 5/4088; A61B 5/7225; A61B 5/7246; G06T 7/0012
See application file for complete search history.

(56) References Cited

U.S. PATENT DOCUMENTS

| | | | |
|---|---|---|---|
| 6,463,315 | B1 | 10/2002 | Klingberg et al. |
| 6,882,876 | B2 | 4/2005 | Ulug |
| 2002/0177760 | A1* | 11/2002 | Ulug ................ G01R 33/56341 600/300 |
| 2013/0223714 | A1 | 8/2013 | Lipton et al. |

OTHER PUBLICATIONS

Dyke et al., "Assessing Disease Severity in Late Infantile Neuronal Ceroid Lipofuscinosis Using Quantitative MR Diffusion-Weighted Imaging" American Journal of Neuroradiology Aug. 2007, 28 (7) 1232-1236 (Year: 2007).*
International Search Report & Written Opinion in International Application No. PCT/US2014/065007, dated Feb. 4, 2015 (9 pages).

* cited by examiner

Table 1. Mean values and standard deviations for all fitting parameters and average MD.

| | $f_{brain}$ | $\mu_{brain}$ (×e-4mm²/s) | $\sigma_{brain}$ (×e-4mm²/s) | $f_{CSF}$ | $\mu_{CSF}$ (×e-3mm²/s) | $\sigma_{CSF}$ (×e-4mm²/s) | $f_{mix}$ | $\theta$ | Average MD |
|---|---|---|---|---|---|---|---|---|---|
| NPH | 0.436±0.043 | 7.87±0.24 | 1.5±0.29 | 0.086±0.022 | 3.2±0.1 | 1.9±0.16 | 0.478±0.061 | 0.57±0.16 | 1.4±0.12 |
| AD | 0.435±0.071 | 7.88±0.25 | 1.5±0.21 | 0.084±0.023 | 3.3±0.3 | 1.5±0.29 | 0.484±0.068 | 0.71±0.14 | 1.5±0.14 |
| PD/DLB | 0.501±0.062 | 8.08±0.35 | 1.6±0.18 | 0.051±0.039 | 3.1±0.2 | 2.1±0.17 | 0.446±0.044 | 0.70±0.12 | 1.3±0.13 |

The table entries are mean ± standard deviation.

FIG. 7

Table A1. Classification power for one-dimensional fitting parameters and binary classifier with group1: NPH and group2: AD.

| | $f_{brain}$ | $\mu_{brain}$ | $\sigma_{brain}$ | $f_{CSF}$ | $\mu_{CSF}$ | $\sigma_{CSF}$ | $f_{mix}$ | $\theta$ | Average MD |
|---|---|---|---|---|---|---|---|---|---|
| Sensitivity | 1.00 | 0.60 | 0.47 | 0.73 | 0.40 | 0.73 | 0.60 | 0.73 | 0.00 |
| Specificity | 0.33 | 0.67 | 0.78 | 0.56 | 0.56 | 0.56 | 0.44 | 0.78 | 1.00 |
| PPV* | 0.71 | 0.75 | 0.78 | 0.73 | 0.60 | 0.73 | 0.64 | 0.85 | 0.00 |
| NPV** | 1.00 | 0.50 | 0.47 | 0.56 | 0.36 | 0.56 | 0.40 | 0.64 | 0.38 |

*Positive Predictive Value (PPV)
**Negative Predictive Value (NPV)

FIG. 8

Table A2. Classification power for one-dimensional fitting parameters and binary classifier with group1: NPH and group2: AD, PD, DLB.

| | $f_{brain}$ | $\mu_{brain}$ | $\sigma_{brain}$ | $f_{CSF}$ | $\mu_{CSF}$ | $\sigma_{CSF}$ | $f_{mix}$ | $\theta$ | Average MD |
|---|---|---|---|---|---|---|---|---|---|
| Sensitivity | 0.87 | 0.93 | 0.53 | 0.87 | 0.60 | 0.73 | 0.73 | 0.73 | 1.00 |
| Specificity | 0.52 | 0.44 | 0.80 | 0.68 | 0.56 | 0.44 | 0.44 | 0.80 | 0.48 |
| PPV* | 0.52 | 0.50 | 0.62 | 0.62 | 0.45 | 0.44 | 0.44 | 0.69 | 0.54 |
| NPV** | 0.87 | 0.92 | 0.74 | 0.89 | 0.70 | 0.73 | 0.73 | 0.83 | 1.00 |

*Positive Predictive Value (PPV)
**Negative Predictive Value (NPV)

FIG. 9

DIAGNOSIS OF NORMAL PRESSURE HYDROCEPHALUS BY AUTOMATED PROCESSING OF MRI IMAGES

CROSS-REFERENCE TO RELATED APPLICATIONS

The present application is a U.S. national phase application under 35 U.S.C. § 371 of International Application No. PCT/US2014/065007, filed on Nov. 11, 2014, which claims the benefit of U.S. Provisional Patent Application No. 61/902,675, filed Nov. 11, 2013, which are each herein incorporated by reference.

FIELD

The present application relates to medical diagnosis and more particularly to diagnosis of normal pressure hydrocephalus.

BACKGROUND

Normal Pressure Hydrocephalus (NPH) is a reversible cause of dementia, incontinence and gait disturbance in the elderly. Accurate and timely diagnosis is essential to its successful treatment. Diagnosis of NPH can be difficult because the clinical symptoms associated with NPH are common in the elderly and can overlap those of age-related neurodegenerative disorders such as Alzheimer's disease (AD) and Parkinson's disease (PD). Non-obstructive enlargement of the cerebral ventricles in NPH can be difficult to distinguish from age and disease related ex-vacuo ventricular enlargement by conventional CT and MRI techniques. Expert clinical evaluations performed in specialized centers can achieve up to 90% accuracy in identifying shunt-responsive NPH patients; however, diagnosis of NPH in general practice is much less successful. It has been estimated recently that only 10% to 20% of patients with NPH get the appropriate specialized treatment. Recognition of NPH in general practice could be improved if more objective and quantitative imaging methods were available for differential diagnostic and prognostic purposes.

Brain imaging is an integral part of NPH diagnosis. To meet the criteria for Probable NPH by international consensus guidelines, brain imaging is used to document an Evans' index (the ratio of the widest diameter of the lateral ventricle's anterior horn to transverse intracranial diameter) of 0.3 or greater. Another imaging sign that has been recently validated as an adjunct to the diagnosis of NPH is disproportionate enlargement of the inferior subarachnoid spaces with tight high-convexity subarachnoid spaces. A number of quantitative imaging biomarkers have also been proposed as aids to NPH diagnosis, such as phase contrast aqueductal flow measurements, aqueductal stroke volume measurements, ventricular volume to cortical thickness ratios, increased Diffusion Tensor Imaging (DTI) fractional anisotropy of periventricular white matter and basal ganglia, cerebrospinal fluid (CSF) and blood flow and temporal changes in the apparent diffusion coefficient during the cardiac cycle. The use of these techniques has largely been confined to research studies in specialty centers and none have been proven to improve the diagnosis of NPH in routine clinical practice.

Alterations in brain water diffusivity in NPH were first reported nearly 20 years ago. It has been recently reported that region-of-interest based DTI techniques can distinguish shunt-responsive NPH from other dementias with higher specificity than the Evans' index (95% versus 80%). Tract-based spatial statistics methods were reported to achieve sensitivity for NPH classification of greater than 90% with specificity between 80% and 85%. However, these methods require operator-defined regions-of-interest, which are subjective and prone to inter-rater variability issues and/or require image registration to normative images. Identifying all registration errors is almost impossible and registration is especially problematic for conditions with large anatomical deformations, such as NPH. Problems with registration of NPH patients have previously been reported.

BRIEF SUMMARY

In an embodiment, a method is disclosed to differentiate NPH from related conditions. The method includes generating a histogram of voxels in an image from a scan of a patient's brain and fitting a curve to the histogram of voxels using a model of brain characteristics. The model comprises at least three functions expressing distribution-groups for voxels and a weighting variable for each of the at least three functions, wherein the at least three functions include a function representing brain tissue, a function representing cerebrospinal fluid (CSF), and a function representing a mix of brain tissue and CSF. The function representing the mix of brain tissue and CSF enables unequal partial volume voxel distributions. The method further includes iteratively changing the function representing the mix of brain tissue and CSF and a variable within the function representing the mix of brain tissue and CSF that represents a relative amount of brain tissue versus CSF mixed in the voxels such that a best fit to the histogram curve is obtained; and comparing the weighting variable for the function representing the mix of brain tissue and CSF to pre-determined values representative of one or more brain conditions or disorders.

In another embodiment, a non-transitory computer-readable medium is disclosed having computer executable instructions for performing operations to differentiate NPH from related conditions, the operations include generating a histogram of voxels in an image from a scan of a patient's brain and fitting a curve to the histogram of voxels using a model of brain characteristics. The model comprises at least three functions expressing distribution-groups for voxels and a weighting variable for each of the at least three functions, wherein the at least three functions include a function representing brain tissue, a function representing cerebrospinal fluid (CSF), and a function representing a mix of brain tissue and CSF. The function representing the mix of brain tissue and CSF enables unequal partial volume voxel distributions. The operations further include iteratively changing the function representing the mix of brain tissue and CSF and a variable within the function representing the mix of brain tissue and CSF that represents a relative amount of brain tissue versus CSF mixed in the voxels such that a best fit to the histogram curve is obtained; and comparing the weighting variable for the function representing the mix of brain tissue and CSF to pre-determined values representative of one or more brain conditions or disorders.

In still another embodiment, a method is disclosed to weight partial voxels in an image of at least two substances, in which the substances intermix. The method includes generating a histogram of voxels in an image of at least two intermixed substances and fitting a curve to the histogram of voxels using a model. The model includes at least three functions expressing distribution-groups for voxels and a weighting variable for each of the at least three functions. The at least three functions include a function representing a first substance, a function representing a second substance, and a function representing a mix of the first and second substances. The function representing the mix of the first and second substances enables unequal partial volume voxel distributions. The method further includes iteratively changing the function representing the mix of the first and second substances and a variable within the function representing the mix of the first and second substances that represents a relative amount of first substance to second substance mixed in the voxels such that a best fit to the curve is obtained; and comparing the weighting variable for the function representing the mix of the first and second substances to predetermined values representative of one or more known mixes.

BRIEF DESCRIPTION OF THE DRAWINGS

The accompanying drawings incorporated in and forming a part of the specification illustrate several aspects of the present invention.

FIG. 7 depicts a table showing mean values and standard deviations for all fitting parameters and average MD in accordance with an illustrative embodiment.

FIG. 8 depicts a table showing classification power for one-dimensional fitting parameters and binary classifier with group 1: NPH and group 2: AD in accordance with an illustrative embodiment.

FIG. 9 depicts a table showing classification power for one-dimensional fitting parameters and binary classifier with group 1: NPH and group 2: AD, PD, DLB in accordance with an illustrative embodiment.

DETAILED DESCRIPTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

As discussed below, radiologic differences between NPH and AD/PD can be captured by a robust and objective Diffusion Tensor Imaging (DTI) technique, which does not require inter-subject image registration or operator-defined regions-of-interest. As discussed below, a parametric fitting model has been developed for the shape of a whole-brain mean diffusivity (MD) histogram applicable in the differential diagnosis of NPH. Histogram approaches are attractive, compared to other diffusion MRI analysis methods, because of their robustness and reproducibility. These approaches typically do not depend on inter-subject registration of images or tissue segmentation and smoothing. Consequently, they are not susceptible to many of the common pitfalls of DTI analysis. NPH is well-suited for MD histogram analysis because transependymal fluid shifts in NPH affect a large number of brain voxels in a way that is directly detectable by MD. The techniques described below capture distinctive features present in the MD histograms of NPH patients.

The pathophysiology of NPH includes alterations in the distribution of water between and within the brain parenchymal and CSF compartments and efforts have been made to diagnose NPH based on those alterations. One possible method involves generating an MD histogram and diagnosing NPH based on parameters generated from the histogram.

Figure 1A:
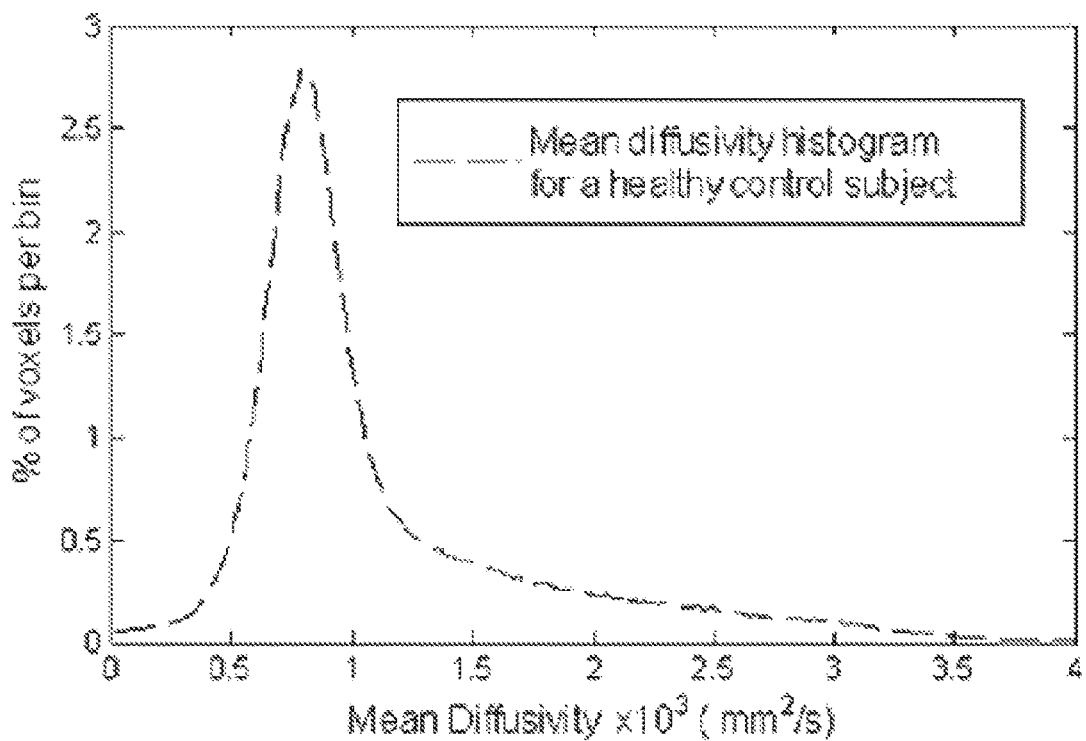
FIG. 1a depicts a mean diffusivity (MD) histogram of a healthy subject in accordance with an illustrative embodiment.
Figure 1B:
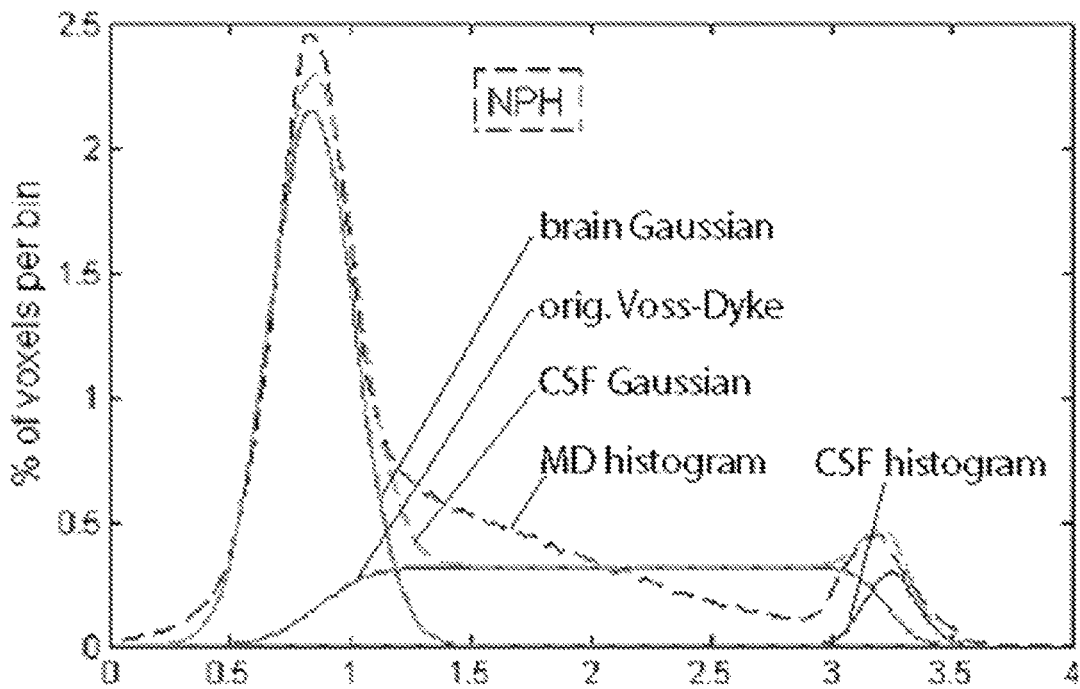
FIG. 1b depicts an MD histogram of an NPH patient that was fitted with the original Voss-Dyke function in accordance with an illustrative embodiment.
Figure 1C:
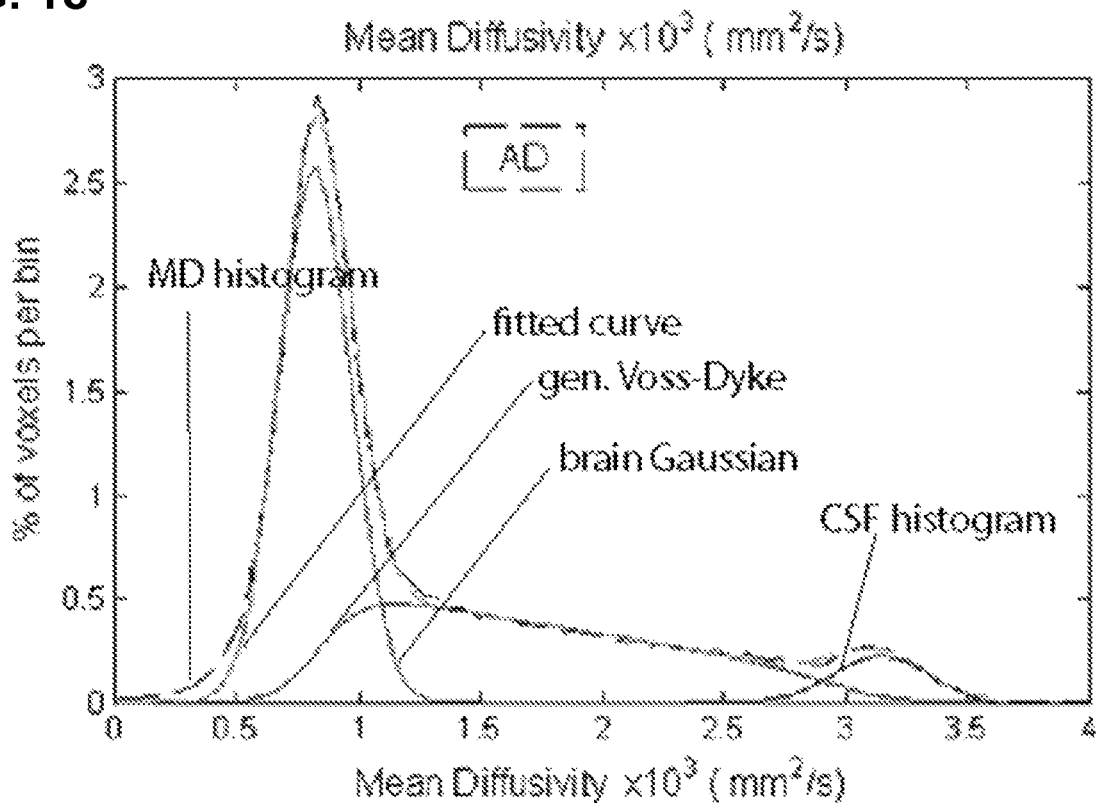
FIG. 1c depicts an MD histogram AD patient that was fitted with the proposed generalized Voss-Dyke function in accordance with an illustrative embodiment.
Figure 1D:
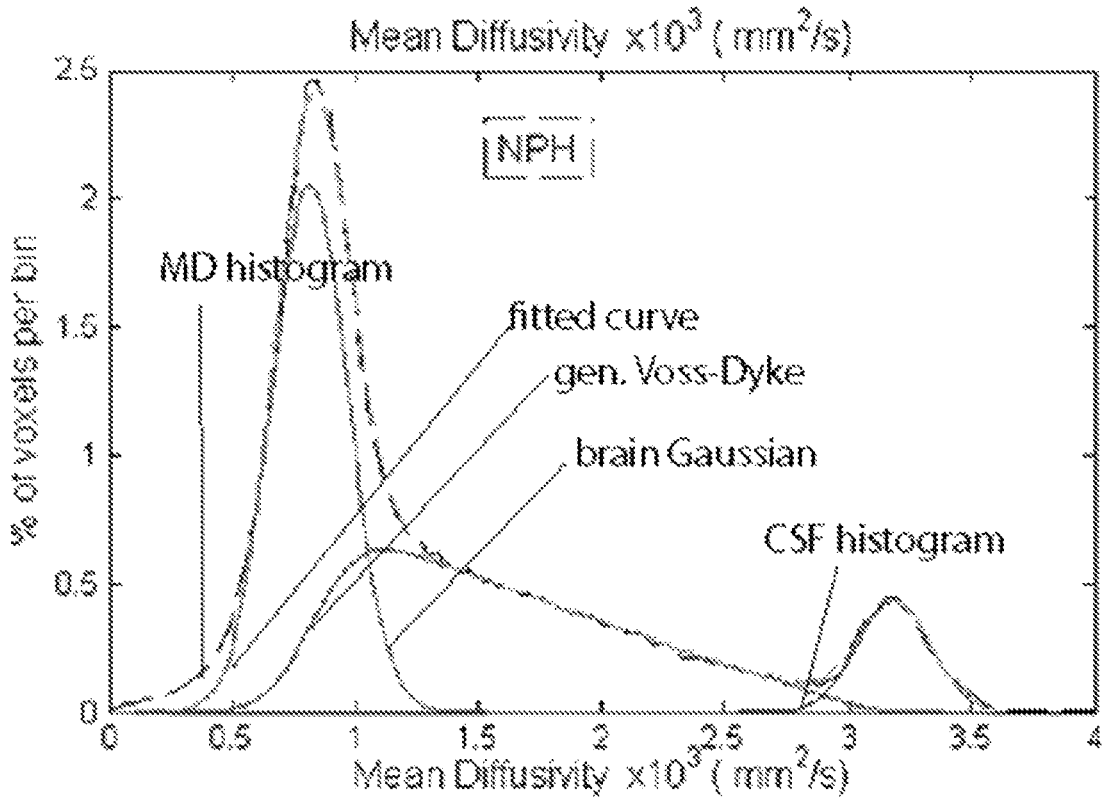
FIG. 1d depicts an MD histogram the NPH patient that was fitted with the proposed generalized Voss-Dyke function in accordance with an illustrative embodiment.

An often-cited downside of the MD histogram approach is CSF "contamination", i.e., inadvertent inclusion into histograms of partial volume voxels with variable amounts of parenchymal and CSF contributions. However, this is actually valuable information for NPH diagnostics, since cerebral atrophy and the abnormal intermingling of free water and brain parenchyma occurs to a pathologic degree in NPH. This can be readily appreciated from a comparison of the MD histograms of a healthy control, an NPH patient and an AD patient as generally depicted in FIGS. 1a-1d. FIG. 1a depicts a mean diffusivity (MD) histogram of a healthy subject in accordance with an illustrative embodiment. FIG. 1b depicts an MD histogram of an NPH patient that was fitted with the original Voss-Dyke function in accordance with an illustrative embodiment. FIG. 1c depicts an MD histogram AD patient that was fitted with the proposed generalized Voss-Dyke function in accordance with an illustrative embodiment. FIG. 1d depicts an MD histogram the NPH patient that was fitted with the proposed generalized Voss-Dyke function in accordance with an illustrative embodiment.

Figure 2:
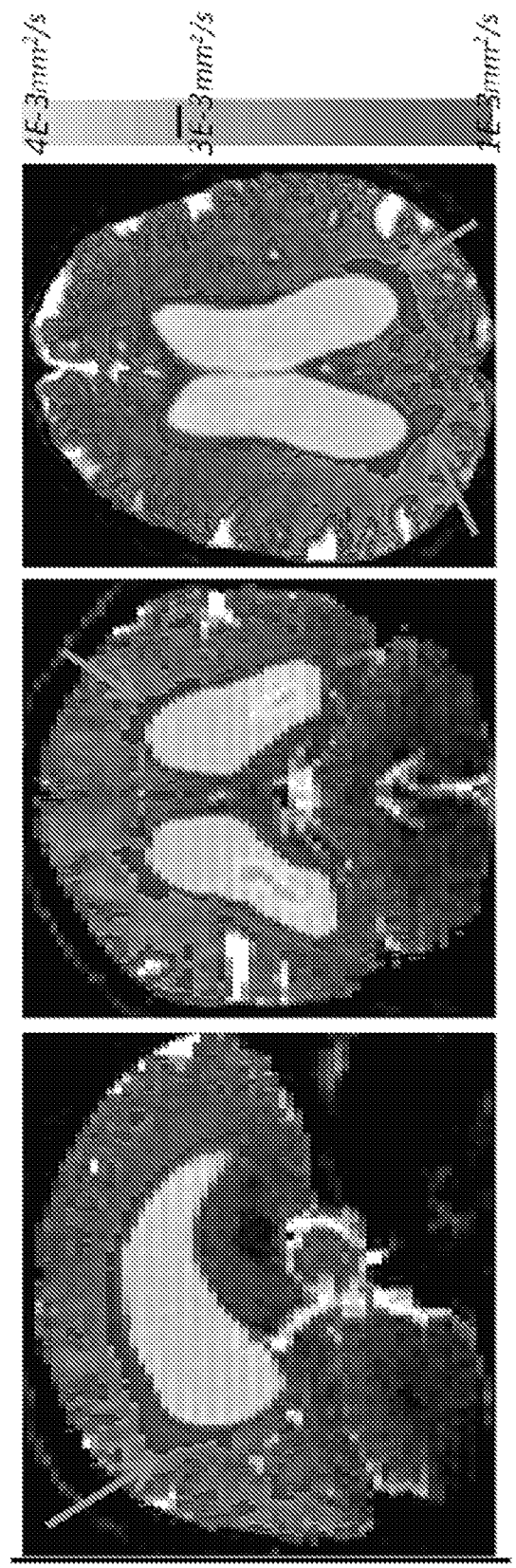
FIG. 2 depicts a magnetic resonance image showing voxels with MD values between 1 E-3 mm$^2$/s and 4 E-3 mm$^2$/s for an NPH patient in accordance with an illustrative embodiment.

As explained in the methods herein, the original Voss-Dyke method operates under the assumption that all partial volume fractions are possible and equally likely. The original Voss-Dyke method adequately modeled MD data from children with Late Infantile Neuronal Lipofuscinosis, in whom ventricle size is actually larger (relative to the brain size) than in the NPH population. Further, as illustrated in FIG. 2, in the case of NPH patients, there are voxels fully within white matter with elevated MD values, but still closer to the MD values for the rest of parenchyma than to the MD values of unrestricted water. FIG. 2 depicts a magnetic resonance image showing voxels with MD values between 1 E-3 $mm^2/s$ and 4 E-3 $mm^2/s$ for an NPH patient in accordance with an illustrative embodiment. Notice the area of increased MD in the periventricular white matter (arrows). Values above 3 E-3 $mm^2/s$ correspond mostly to ventricles, whereas values below 1 E-3 $mm^2/s$ are primarily within the brain parenchyma (shown in grey), a histogram of a typical normal individual. Accordingly, better modeling is achieved with the generalized form of the Voss-Dyke function described herein.

Figure 3:
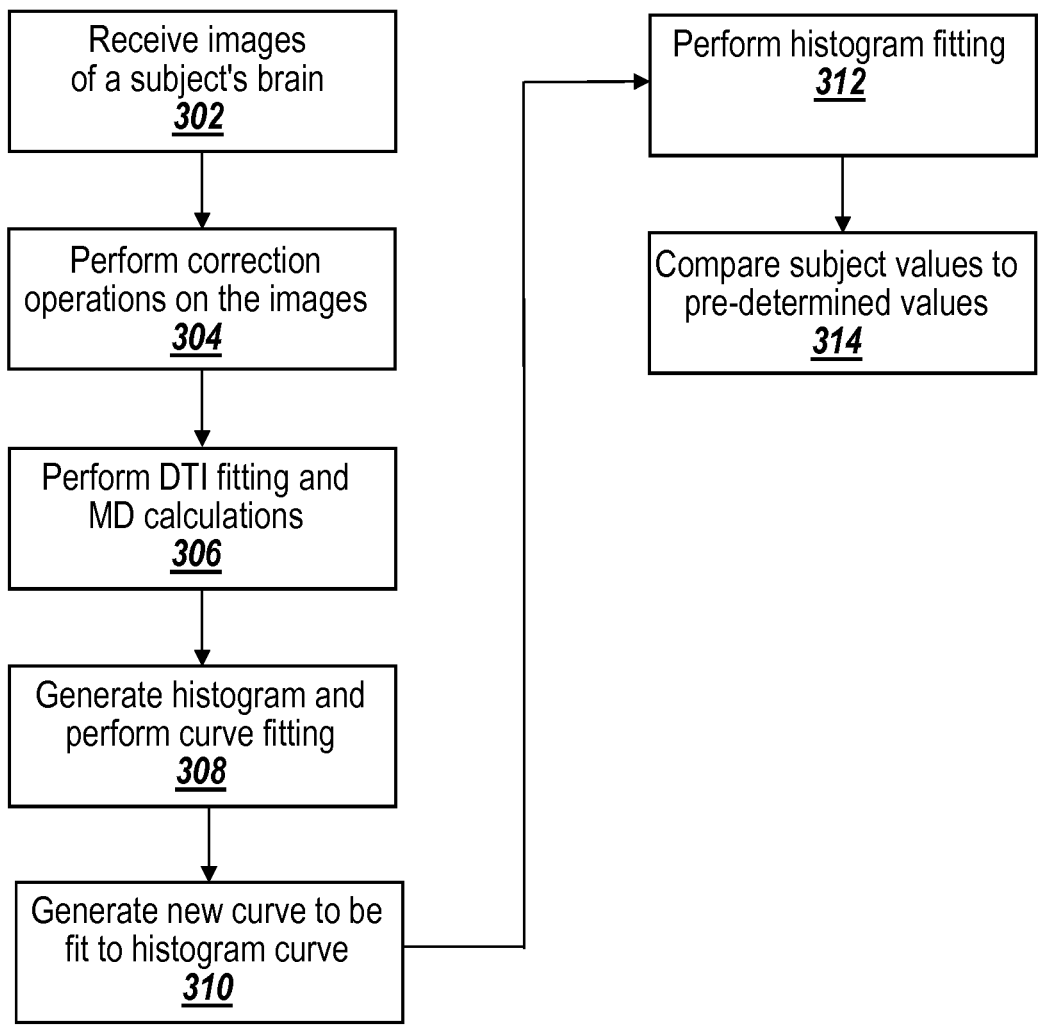
FIG. 3 is a flow diagram of a method for determining brain-related conditions in accordance with an illustrative embodiment.

FIG. 3 is a flow diagram of a method for determining brain-related conditions in accordance with an illustrative embodiment. In an operation 302, diffusion tensor imaging (DTI) images are received of a subject's brain. In an embodiment, the DTI images are obtained using equipment capable of DTI imaging. The images received of the subject's brain include a set of three-dimensional, orientation independent diffusion-weighted images of the brain. In an embodiment, data and images may be collected for both normal and diseased-patients and stored in a database for future comparison with a current patient to aid in diagnosis of a condition or disease.

The DTI image file, along with the image file acquired without diffusion weighting, is transferred from the scanner to a separate processor or computer configuration. The scanner processor could also be employed for this processing, and the invention is intended to cover both alternatives. The invention is operational with numerous other general purpose or special purpose processors or computer configurations. Examples of well-known processors and/or computer configurations that may be suitable for use with the invention include, but are not limited to, an imaging workstation, personal computers, server computers, hand-held or laptop devices, multiprocessor systems, microprocessor-based systems, network PCs, minicomputers, mainframe computers, peripherals (e.g., scanner, data acquisition system, video card, network interface card, etc.) and the like. Programs operating on the processor are generally stored on computer readable media. Computer readable media can be any available media that can be accessed by the processor and includes both volatile and nonvolatile media, removable and non-removable media. By way of example, and not limitation, computer readable media may comprise computer storage media and communication media. Computer storage media includes non-transitory, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the processor, all or some of which may be local, or provided in the cloud. By way of example, and not limitation, communication media includes wired media such as a wired network or direct-wired connection, and wireless media such as acoustic, RF, infrared and other wireless media. Combinations of the any of the above should also be included within the scope of computer readable media. In addition, the operations may be performed to by special purpose hardware and/or software modules.

In an operation 304, the DTI images and/or the MRI images may optionally be corrected. For example, eddy current correction and motion correction may be performed by linear registration of the gradient volumes to low gradient ("$b_0$") volume followed by corresponding adjustment of the encoding vectors. In an embodiment, the portion of the image representing the skull may be removed. For example, automatic skull stripping may be executed, and may be followed by manual corrections where needed.

In an operation 306, DTI fitting and MD calculations are performed by means known in the art to produce MD values. In an embodiment, operation 306 involves converting the three-dimensional data from the images to two-dimensional data (e.g., the MD values).

In an operation 308, an orientation independent diffusion histogram is generated using the MD values and curve fitting is performed on the histogram. In an embodiment, the MD values from operation 306 are placed in histogram bins. There may be various numbers of pins depending on the embodiment, e.g., from 10 to 1000 bins, 100 to 800 bins, 250 bins, etc. In an embodiment, the histogram is normalized and unit area is used. In addition, the histogram is mapped directly onto a smooth curve (the "histogram curve").

In an operation 310, a new curve is generated that is to be fit to the histogram curve. In an embodiment, generation of the new curve includes fitting the two-dimensional data of the histogram to a model that has a good fit to actual brain characteristics. For example, the new curve may be a sum of functions with fitting parameters that are generated using the parametric model discussed below.

The parametric model for fitting the histograms is a modification of a multicomponent model for analyzing pediatric DTI data. The histogram curve is fitted by a sum of at least 3 functions, with three of the functions representing the brain, CSF, and the brain-CSF partial volume voxels, respectively. The functions may be weighted. In addition, the functions may be Gaussian. In an embodiment, the new curve to be fitted to the histogram curve is represented by the following equation:

$$P(MD) = f_{brain} P_{brain}(MD) + f_{CSF} P_{CSF}(MD) + f_{mix} P_{VD}(MD)$$

where $$P_{brain}(MD) = \frac{1}{\sqrt{2\pi}\, \sigma_{brain}} \exp\left[\frac{-1}{2}\left(\frac{MD - \mu_{brain}}{\sigma_{brain}}\right)^2\right]$$

$$P_{CSF}(MD) = \frac{1}{\sqrt{2\pi}\, \sigma_{CSF}} \exp\left[\frac{-1}{2}\left(\frac{MD - \mu_{CSF}}{\sigma_{CSF}}\right)^2\right]$$

and, the Generalized Voss-Dyke function:

$$P_{VD}(MD) = \int_0^1 \frac{1}{\sqrt{2\pi}\, \sigma_\theta(t)} \exp\left[\frac{-1}{2}\left(\frac{MD - \mu_\theta(t)}{\sigma_\theta(t)}\right)^2\right] dt$$

-continued where $\mu_\theta(t) =$ $$t^\theta \mu_{brain} + (1-t^\theta)\mu_{CSF} \text{ and } \sigma_\theta(t) = \sqrt{t^{2\theta}\sigma_{brain}^2 + (1-t^\theta)^2\sigma_{CSF}^2}.$$

In this embodiment, the three functions include: 1) $f_{brain}P_{brain}(MD)$; 2) $f_{CSF}P_{CSF}(MD)$; and 3) $f_{CSF}P_{CSF}(MD)$. Here $f_{brain}$, $f_{CSF}$ and $f_{mix}$, correspond to histogram fractions of brain parenchyma, CSF and mixed voxels, respectively, and act as weighting factors. $\mu_{brain}$ and $\sigma_{brain}$ ($\mu_{CSF}$, $\sigma_{CSF}$) are the mean and standard deviation of the brain or CSF Gaussian as per their labels. The parameter $\theta$ did not exist in the original Voss-Dyke equation and is introduced here. The parameter $\theta$ encodes the slope of the Generalized Voss-Dyke function, as explained below.

Figures 4A, 4B, 4C:
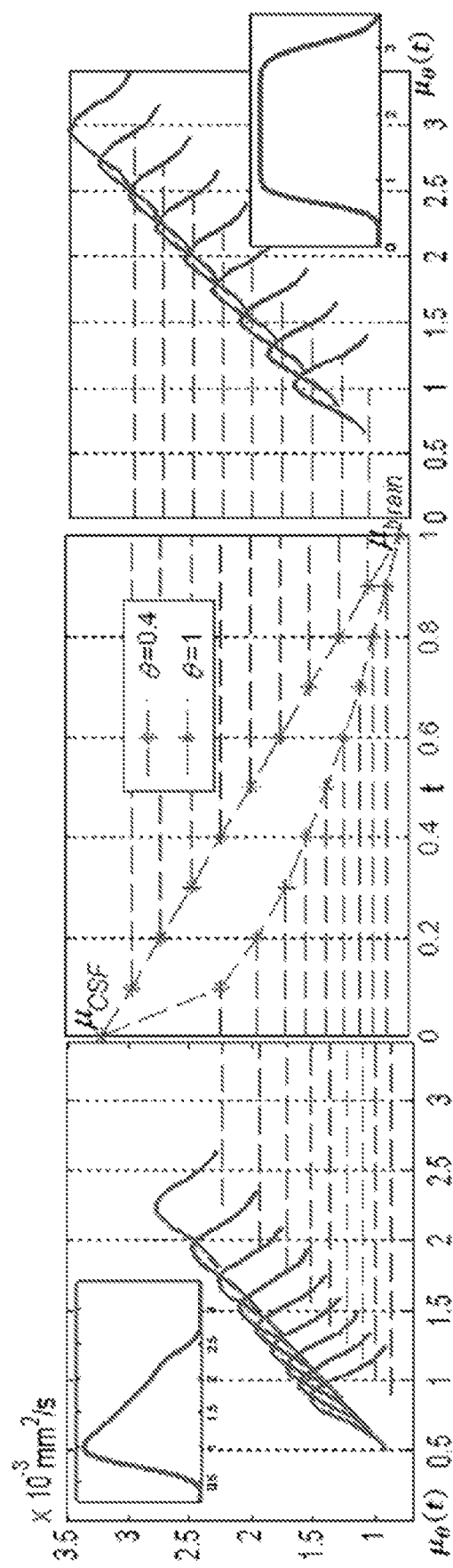
FIG. 4a depicts a graph showing the generalized Voss-Dyke function resulting as a sum of corresponding Gaussians in accordance with an illustrative embodiment.
FIG. 4b depicts a graph showing the homotopy mapping $\mu_\theta(t) = t^\theta \mu_{brain} + (1-t^\theta) \mu_{CSF}$ in accordance with an illustrative embodiment.
FIG. 4c depicts a graph showing the original Voss-Dyke function resulting as a sum of corresponding Gaussians in accordance with an illustrative embodiment.

The integral on the unit interval in the definition of the Generalized Voss-Dyke function $P_{VD}(MD)$ may be approximated by a quadrature, for example a Gaussian quadrature or any quadrature known in the art, and said quadrature may be on various numbers of points based on the embodiment, e.g., 10 to 1000 points, 50 to 500 points, 100 points, etc. For example, this integral can be thought of as a sum of Gaussian distributions representing a homotopy from the Gaussian function $P_{CSF}(MD)$ to the Gaussian function $P_{brain}(MD)$. In the Generalized Voss-Dyke function, smaller values of $\theta$ indicate a higher percentage of voxels with MD values close to that of the brain. This parameter creates the possibility of achieving unequal partial volume voxel distributions. FIG. 4c depicts a graph showing the original Voss-Dyke function resulting as a sum of corresponding Gaussians in accordance with an illustrative embodiment. As illustrated in FIG. 4c, in the original Voss-Dyke function, all fractions of partial volume voxels are necessarily equally likely. The insert in the graph of FIG. 4c represents the original Voss-Dyke functions resulting as the sum of the corresponding Gaussians.

FIG. 4a depicts a graph showing the generalized Voss-Dyke function resulting as a sum of corresponding Gaussians in accordance with an illustrative embodiment. In the example at hand, $\theta=0.4$, and the intermediate distributions are skewed towards $P_{brain}(MD)$, giving the slope to the generalized Voss-Dyke function. The inserts in the graph represents the generalized Voss-Dyke functions resulting as the sum of the corresponding Gaussians. FIG. 4b depicts a graph showing the homotopy mapping $\mu_\theta(t)=t^\theta\mu_{brain}+(1-t^\theta)\mu_{CSF}$ in accordance with an illustrative embodiment.

Figure 10:
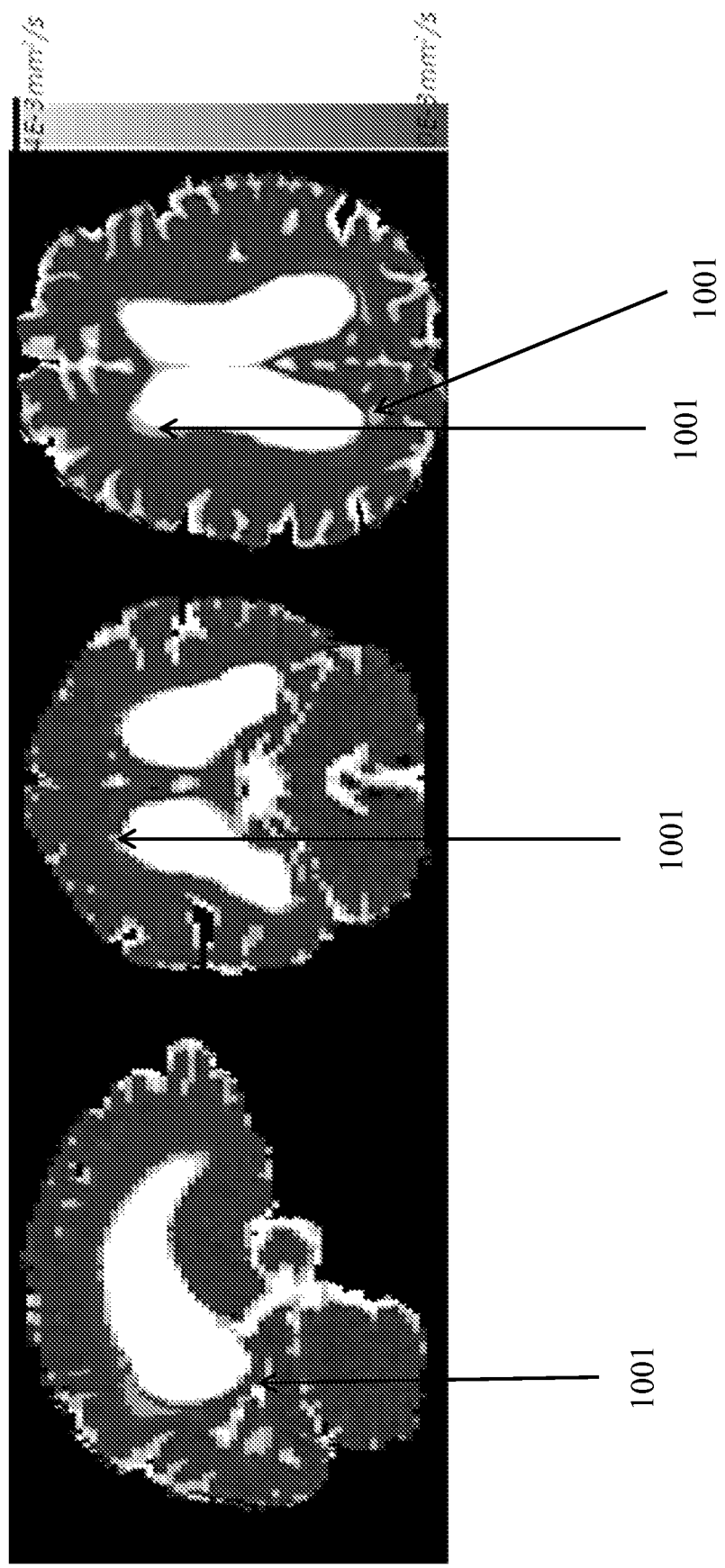
FIG. 10 depicts MRI images showing MD distribution for an NPH patient in accordance with an illustrative embodiment.

FIG. 10 depicts MRI images showing MD distribution for an NPH patient in accordance with an illustrative embodiment. FIG. 10 includes areas of increased MD 1001 in the periventricular white matter, which is a result of pathologic water accumulation and is characteristic of NPH. In a patient without pathologic water accumulation in their brain, the distribution of partial volume voxels is generally homogenous which leads to a flat curve for the generalized Voss-Dyke function similar to the original Voss-Dyke function depicted in the graph insert of FIG. 4c. In contrast, in a patient with pathologic water accumulation as depicted in FIG. 10, the distribution of partial volume voxels is disturbed such that the distribution is not equal or homogenous. The generalized Voss-Dyke function discussed above enables such a distribution to be appropriately modeled. Indeed, using the generalized Voss-Dyke function, such a distribution would lead to a curve similar to that depicted in the graph insert of FIG. 4a.

NPH patients have a disproportionally high number of voxels with elevated MD values (but lower than that of the free water in the CSF compartment). AD and PD patients, on the other hand, have an increased number of partial volume voxels (higher $f_{mix}$) and a more proportional distribution of those voxels (higher $\theta$). This results in a steeper slope of the middle part of the histogram fit for NPH patients compared to AD and PD (see FIG. 1) and may therefore be used, directly or indirectly, to distinguish NPH patients from AD and PD.

The form of the Generalized Voss-Dyke function $P_{VD}(MD)$ may be chosen, as it is above, so that the function $P(MD)$ is differentiable with respect to $\theta$, as it is with the respect to the other fitting parameters, so the Jacobian is defined.

In an embodiment, the total number of optimization parameters was eight: $f_{brain}$, $f_{CSF}$, $f_{mix}$, $\mu_{brain}$, $\mu_{CSF}$, $\sigma_{brain}$, and $\sigma_{CSF}$ and $\theta$. If too many optimization parameters are chosen, there is a danger of overfitting.

Histogram fitting is performed in an operation 312. In an embodiment, histogram fitting may be performed by software based on the Levenberg-Marquardt algorithm or by any other means known to those in the art. The fitting may be iterated until the difference in fitted curves between two consecutive iterations is less than a given value, which may vary based on the embodiment, e.g., between zero and 5%, between 0.01% and 2%, about 0.1%, etc. The result may be considered to fit adequately, for example, if the absolute difference between a subject's measured histogram and fitted curve is less than a given percentage of the total measured data, for example between 0% and 20%, or between 1% and 10%, 5%, etc.

In an embodiment, the Levenberg-Marquardt algorithm is iterated until the difference in fitted curves between two consecutive iterations is less than 0.1% and is considered to fit adequately if the absolute difference between subject's measured histogram and fitted curve is less than 5% of the total measured data.

Figure 5:
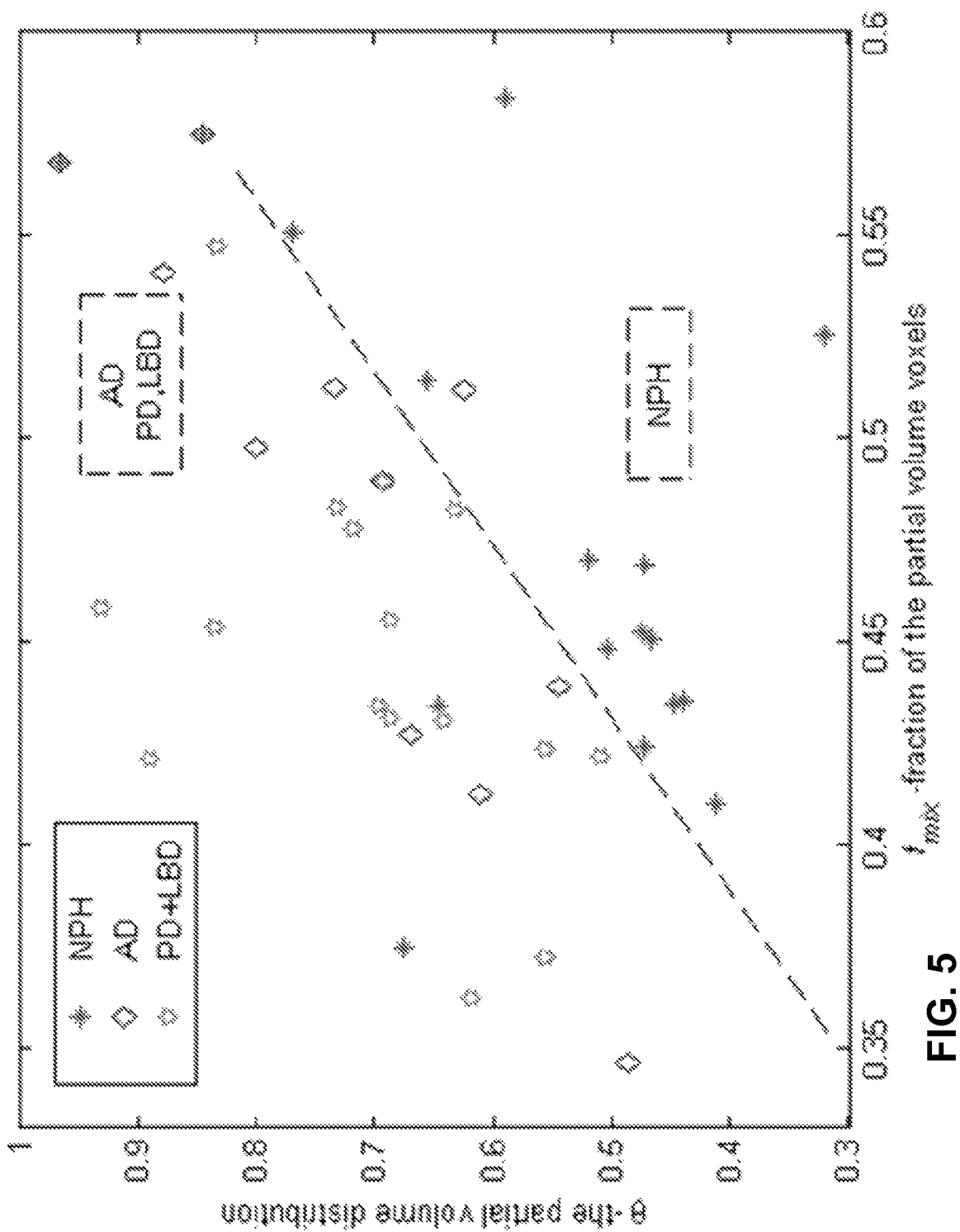
FIG. 5 depicts a graph showing a fraction of the mid-range MD voxels ($f_{mix}$) versus $\theta$ in accordance with an illustrative embodiment.

In an operation 314, parameters associated with a subject's curve are compared to values that have been pre-determined to likely indicate a disease or condition. In an embodiment, fitting parameters $\theta$ and $f_{mix}$ are plotted on a graph with a curve signifying a cut-off between a subject likely to have NPH and a subject likely to have other diseases or conditions. For example, FIG. 5 depicts a graph showing a fraction of the mid-range MD voxels ($f_{mix}$) versus $\theta$ in accordance with an illustrative embodiment. Lower values of $\theta$ indicate a higher number of voxels with MD values closer to parenchyma MD values and a lower number of the voxels with MD values closer to CSF. The classification line presented on the graph is: $\theta_{cut}=-0.4+2.1*f_{mix}$. The curve may be refined with time, as more data is acquired. Applying the method described above with respect to FIG. 3, the curve depicted in FIG. 5 can clinically distinguish probable NPH from Alzheimer's Disease (AD), Parkinson's Disease (PD), and Lewy Body Dementia (LBD) with 86% sensitivity and 96% specificity. The technique yielded 86% sensitivity and 88% specificity when differentiating NPH from Alzheimer's Disease only. The placement of a subject's data on the graph will inform a clinician's determination of the patient's disease or condition.

To summarize the method, a database is collected of normal and diseased-patient data against which data for which information helpful to diagnosis is to be compared. The data for the control subjects and the to-be diagnosed patients is processed in the same way, as follows. A set of three-dimensional diffusion-weighted images of the brain are obtained. From the images, orientation independent diffusion-weighted images are provided. Those orientation independent diffusion-weighted images are then processed to obtain orientation independent diffusion histograms of the entire brain. Thus, the three-dimensional data from the images is now reduced to two-dimensional data. The orientation independent average diffusion maps are, in effect, histograms of the diffusion constants taken from the entire brain. As the third step, the two-dimensional data is then fit to a model. In this particular case a model which has a good fit to the actual brain characteristics is used. From the model, the weighting variable for the mixed fraction $f_{mix}$ and relative amount of brain tissue vs CSF mixed in the partial voxels θ are determined. Those parameters for a patient being diagnosed are compared to the parameters previously collected for AD, PD, and DLB and can inform a neurologist's decision regarding the patient diagnosis.

The diagnosis of NPH is a clinical diagnosis and it can be made by a neurologist anytime during the course of the disease. A gold standard in diagnosing NPH is to perform a spinal tap test and see if the patient improves afterwards. The spinal tap test basically removes some of the fluid that may be causing NPH. Typically, if a patient receives a spinal tap test and improves afterwards, the patient is diagnosed as having NPH. Some patients do improve after the spinal tap test for extended period of times. Normally the improvement is short-lived and patient needs to be shunted for long term improvement. In clinical practice the diagnosis of NPH is complicated. This is particularly true in elderly patients with shunt failure where ventricular size and morphology may not be diagnostic.

The method of the present invention can also be used in monitoring treatment response in shunted patients. In successfully treated patients, the measured parameters, the weighting variable for the mixed fraction $f_{mix}$, and relative amount of brain tissue to CSF mixed in the voxels θ would normalize. In patients where treatment was not optimal (e.g., shunt malfunction, disabled-shunt, etc.), the measured values would be not-normal.

Once a diagnosis is made and treatment has been initiated, the treatment response of patients can be monitored by tracking the measured parameters over time. If the weighting variable for the mixed fraction $f_{mix}$ and relative amount of brain tissue vs CSF mixed in the voxels θ are approaching the characteristic of the normal group, the treatment is on track. If measured parameters move away from the characteristic of the normal group provides an alert that the patient is not responding to the treatment.

Mixed-Voxel Weighting Determination

The method provided herein may be used to better estimate the quantity of substances contributing to mixed voxels (or for two-dimensional images, pixels—"voxels" shall be interpreted as meaning voxel or pixel as needed) in any image.

The methods have utility in MRI medical imaging, as described herein, as well as in other forms of medical imaging, such as X-ray, CT scanning, ultrasound, PET, SPECT, etc. The methods have utility in any field where information must be extracted from remotely sensed imagery, including spectral imagery. For example and without limitation, analysis of satellite and airborne image data is useful to conduct studies and to monitor natural and man-made conditions and phenomena in fields as diverse as zoning and land management, weather forecasting, environmental monitoring, disaster assessment response (e.g., oil spills, forest fires, warfare, etc.).

In an embodiment, images are taken of a subject comprising at least two substances that intermix. The image file is transferred from the image acquisition apparatus to a separate processor or computer configuration. The processor of the acquisition apparatus could also be employed for this processing, and the invention is intended to cover both alternatives. The invention is operational with numerous other general purpose or special purpose processors or computer configurations. Examples of well-known processors and/or computer configurations that may be suitable for use with the invention include, but are not limited to, an imaging workstation, personal computers, server computers, hand-held or laptop devices, multiprocessor systems, microprocessor-based systems, network PCs, minicomputers, mainframe computers, peripherals (e.g., scanner, data acquisition system, video card, network interface card, etc.) and the like. Programs operating on the processor are generally stored on computer readable media. Computer readable media can be any available media that can be accessed by the processor and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the processor, all or some of which may be local, or provided in the cloud. By way of example, and not limitation, communication media includes wired media such as a wired network or direct-wired connection, and wireless media such as acoustic, RF, infrared and other wireless media. Combinations of the any of the above should also be included within the scope of computer readable media.

The images may be corrected as is known in the art.

The intensity of each voxel is placed in histogram bins. There may be from 10 to 1000 bins, 100 to 800 bins, or 250 bins. In an embodiment, the histogram is normalized and unit area is used. The histogram is mapped directly onto a smooth curve (the "histogram curve"), by means known in the art.

Next, a new curve is generated that is fit to the histogram curve. The new curve is a sum of functions with fitting parameters.

The histogram curve is fitted by a sum of at least 3 functions, with three of the functions representing substance 1, substance 2, and the substance 1,2 partial volume voxels. The functions may be weighted. The functions may be Gaussian. For example:

$$P(MD) = f_1 P_1(MD) + f_2 P_2(MD) + f_{1,2} P_{1,2}(MD)$$

where $$P_1(MD) = \frac{1}{\sqrt{2\pi}\,\sigma_1} \exp\left[\frac{-1}{2}\left(\frac{MD - \mu_1}{\sigma_1}\right)^2\right]$$

$$P_2(MD) = \frac{1}{\sqrt{2\pi}\,\sigma_2} \exp\left[\frac{-1}{2}\left(\frac{MD - \mu_2}{\sigma_2}\right)^2\right]$$

and, the Generalized Voss-Dyke function:

$$P_{1,2}(MD) = \int_0^1 \frac{1}{\sqrt{2\pi}\,\sigma_\theta(t)} \exp\left[\frac{-1}{2}\left(\frac{MD - \mu_\theta(t)}{\sigma_\theta(t)}\right)^2\right] dt$$

where $\mu_\theta(t) = t^\theta \mu_1 + (1-t^\theta)\mu_2$ and $\sigma_\theta(t) = \sqrt{t^{2\theta}\sigma_1^2 + (1-t^\theta)^2 \sigma_2^2}$.

Here $f_1$, $f_2$ and $f_{1,2}$ correspond to histogram fractions of substance 1, substance 2 and mixed voxels respectively and act as weighting factors; $\mu_1$ and $\sigma_1$ ($\mu_2$, $\sigma_2$) are the mean and standard deviation of the substance 1 or substance 2 Gaussian as per their labels. The parameter $\theta$ did not exist in the original Voss-Dyke equation and is introduced here, this parameter encodes the slope of the Generalized Voss-Dyke function, as explained below.

The integral on the unit interval in the definition of the Generalized Voss-Dyke function $P_{1,2}(MD)$, may be approximated by a quadrature, for example a Gaussian quadrature or any quadrature known in the art, and said quadrature may be on 10 to 1000 points, 50 to 500 points, or 100 points. For example, this integral can be thought of as a sum of Gaussian distributions representing a homotopy from the Gaussian function $P_2(MD)$ to the Gaussian function $P_1(MD)$. In the Generalized Voss-Dyke function, smaller values of $\theta$ indicate a higher percentage of voxels with MD values close to that of the substance 1. This parameter creates the possibility of achieving unequal partial volume voxel distributions.

The form of the Generalized Voss-Dyke function $P_{1,2}(MD)$ may be chosen, as it is above, so that the function $P(MD)$ is differentiable with respect to $\theta$, as it is with the respect to the other fitting parameters, so the Jacobian is defined.

In an embodiment, the total number of optimization parameters is eight: $f_1$, $f_2$, $f_{1,2}$, $\mu_1$, $\mu_2$, $\sigma_1$, $\sigma_2$ and $\theta$. If too many optimization parameters are chosen, there is a danger of overfitting.

Histogram fitting is then performed, and may be performed by many means known in the art. In an embodiment, it may be performed by software based on the Levenberg-Marquardt algorithm. The fitting may be iterated until the difference in fitted curves between two consecutive iterations is less than a given value, which may be between zero and 5%, or between 0.01% and 2%, or may be 0.1%, and the result may be considered fitting adequately by means known in the art; for example, if the absolute difference between subjects' measured histogram and fitted curve is less than a given percentage of the total measured data, for example between 0% and 20%, or between 1% and 10%, or 5%.

In an embodiment, the Levenberg-Marquardt algorithm is iterated until the difference in fitted curves between two consecutive iterations is less than 0.1% and is considered fitting adequately if the absolute difference between subjects' measured histogram and fitted curve is less than 5% of the total measured data.

The following statements are potential claims that may be converted to claims in a future application. No modifications of the following statements should be allowed to affect the interpretation of claims which may be drafted when this provisional application is converted into a regular utility application.

Examples

The present description is further illustrated by the following examples, which should not be construed as limiting in any way. The contents of all cited references (including literature references, issued patents, published patent applications as cited throughout this application) are hereby expressly incorporated by reference.

The clinical diagnoses were established by two neurologists (N. R. and M. L. with 21 and 16 years of experience, respectively). Probable idiopathic NPH was diagnosed in accordance with the international consensus guidelines. AD, PD, and Dementia with Lewy Body were diagnosed in accordance with published criteria. The subjects of this study included 15 probable idiopathic NPH patients (7 female and 8 male, mean age 77.0, age range 63-89), 9 AD patients (5 female and 4 male, mean age 77.2, age range 63-85), and 16 patients with either PD or DLB (7 female and 9 male, mean age 73.6, age range 51-86). Two additional subjects diagnosed with a combination of NPH and AD were also included (women, ages 77 and 78). All NPH patients had an Evans' index greater than or equal to 0.3. All but two AD patients also had an Evans' index greater than or equal to 0.3. Five out of sixteen non-NPH, non-AD patients had an Evans' index greater than 0.3.

Subjects with secondary NPH, obstructive hydrocephalus or shunts were not considered. Five patients with infarcts greater than 1 cm in major vascular territories were excluded. Lacunes and smaller infarcts were not exclusionary, as this comorbidity is frequently present in suspected NPH patients.

Image Acquisition and Preprocessing

Diffusion weighted MRI were acquired on a 3T GE Signa EXCITE scanner, using 33 direction echo-planar diffusion weighted scans at b=1000 s/mm2 and one at b=0 s/mm2. TE was 70-80 ms, TR 8.2 s. The brain was covered with 60 2.5 mm thick slices with no gaps between slices. The voxel size was 1.8×1.8×2.5 mm³.

Eddy current correction and motion correction were performed by linear registration of the gradient volumes to low gradient ("b0") volume followed by corresponding adjustment of the encoding vectors. The automatic skull stripping was followed by manual corrections where needed. DTI fitting and MD calculations were performed in FSL. MD values were placed in the 250 bins of normalized histograms with unit area and a curve was fitted to the histogram.

Analysis Methods

The normalized histograms were fitted by a weighted sum of 3 functions representing the brain, CSF and the brain-CSF partial volume voxels together with brain voxels with high MD:

$$P(MD) = f_{brain} P_{brain}(MD) + f_{CSF} P_{CSF}(MD) + f_{mix} P_{VD}(MD)$$

where $$P_{brain}(MD) = \frac{1}{\sqrt{2\pi}\,\sigma_{brain}} \exp\left[\frac{-1}{2}\left(\frac{MD - \mu_{brain}}{\sigma_{brain}}\right)^2\right]$$

$$P_{CSF}(MD) = \frac{1}{\sqrt{2\pi}\,\sigma_{CSF}} \exp\left[\frac{-1}{2}\left(\frac{MD - \mu_{CSF}}{\sigma_{CSF}}\right)^2\right]$$

and the Generalized Voss-Dyke function:

$$P_{VD}(MD) = \int_0^1 \frac{1}{\sqrt{2\pi}\,\sigma_\theta(t)} \exp\left[\frac{-1}{2}\left(\frac{MD - \mu_\theta(t)}{\sigma_\theta(t)}\right)^2\right] dt$$

where $\mu_\theta(t) = t^\theta \mu_{brain} + (1-t^\theta)\mu_{CSF}$ and $\sigma_\theta(t) = \sqrt{t^{2\theta}\sigma_{brain}^2 + (1-t^\theta)^2 \sigma_{CSF}^2}$.

Here $f_{brain}$, $f_{CSF}$ and $f_{mix}$, correspond to histogram fractions of brain parenchyma, CSF and mixed voxels respectively; $\mu_{brain}$ and $\sigma_{brain}$ ($\mu_{CSF}$, $\sigma_{CSF}$) are the mean and standard deviation of the brain (CSF) Gaussian.

The integral on the unit interval in the definition of the Generalized Voss-Dyke function $P_{VD}(MD)$, was approximated by a Gaussian quadrature on 100 points. This integral can be thought of as a sum of 100 Gaussian distributions representing a homotopy from the Gaussian function $P_{CSF}(MD)$ to the Gaussian function $P_{brain}(MD)$. Smaller values of $\theta$ indicate a higher percentage of voxels with MD values close to that of the brain. This parameter creates the possibility of achieving unequal partial volume voxel distributions. As discussed above, in the original Voss-Dyke function, all fractions of partial volume voxels are necessarily equally likely.

NPH patients have a disproportionally high number of voxels with elevated MD values (but lower than that of the free water in the CSF compartment). AD and PD patients, on the other hand, have an increased number of partial volume voxels (higher $f_{mix}$) and a more proportional distribution of those voxels (higher $\theta$). This results in a steeper slope of the middle part of the histogram fit for NPH patients compared to AD and PD and may be used to distinguish NPH patients from AD and PD.

The form of the function $P_{VD}(MD)$ was chosen so that the function $P(MD)$ is differentiable with respect to $\theta$, as it is with the respect to the other fitting parameters, so the Jacobian is defined. The total number of optimization parameters was eight: $f_{brain}$, $f_{CSF}$, $f_{mix}$, $\theta_{brain}$, $\mu_{CSF}$, $\sigma_{brain}$, $\sigma_{CSF}$ and $\theta$.

Histogram fitting was performed by in-house developed software based on the Levenberg-Marquardt algorithm. The Levenberg-Marquardt algorithm was iterated until the difference in fitted curves between two consecutive iterations was less than 0.1% and considered fitting adequately (successfully) if the absolute difference between subjects' measured histogram and fitted curve is less than 5% of the total measured data.

Fitting parameters $\theta$ and $f_{mix}$ were used to construct two-dimensional linear classifiers, one comparing NPH to AD only (group1: NPH, group2: AD) and another comparing NPH to all other conditions (group1: NPH, group2: AD, PD, DLB). ROC analysis was performed with a publically available MATLAB package. The reported sensitivity and specificity values are those that maximize Youden's index.

Binary classifiers based on all 8 fitting parameters and average MD over the whole brain were considered.

RESULTS

The Generalized Voss-Dyke fitting was successful for all subjects (i.e., the absolute difference between subject's measured histogram and fitted curve was less than 5% of the total measured histogram). Statistics on all of the fitting parameters and average MD (over the whole histograms) are depicted in the table of FIG. 7.

Classification Power

We compared two variants of binary classifiers: (1) comparing NPH patients to AD patients only and (2) comparing NPH patients to all other patient groups jointly (group 1: NPH, group 2: AD, PD, DLB). The two patients diagnosed both with NPH and AD were excluded from classification analysis.

Figure 6B:
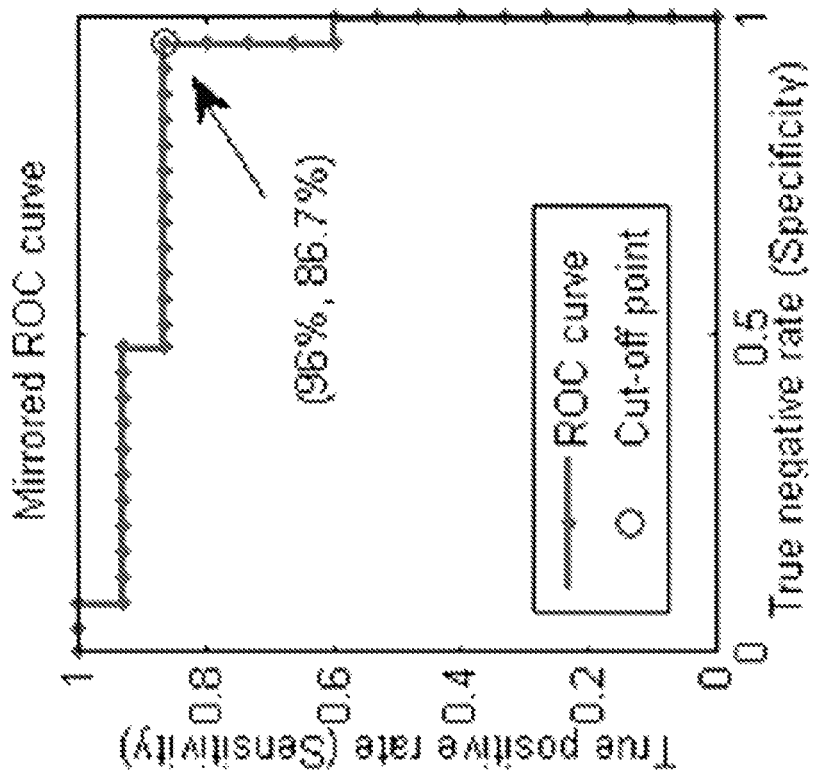
FIG. 6b depicts a graph showing an ROC curve for NPH patient classification against joint AD, PD and LBD patient group in accordance with an illustrative embodiment.
Figure 6A:
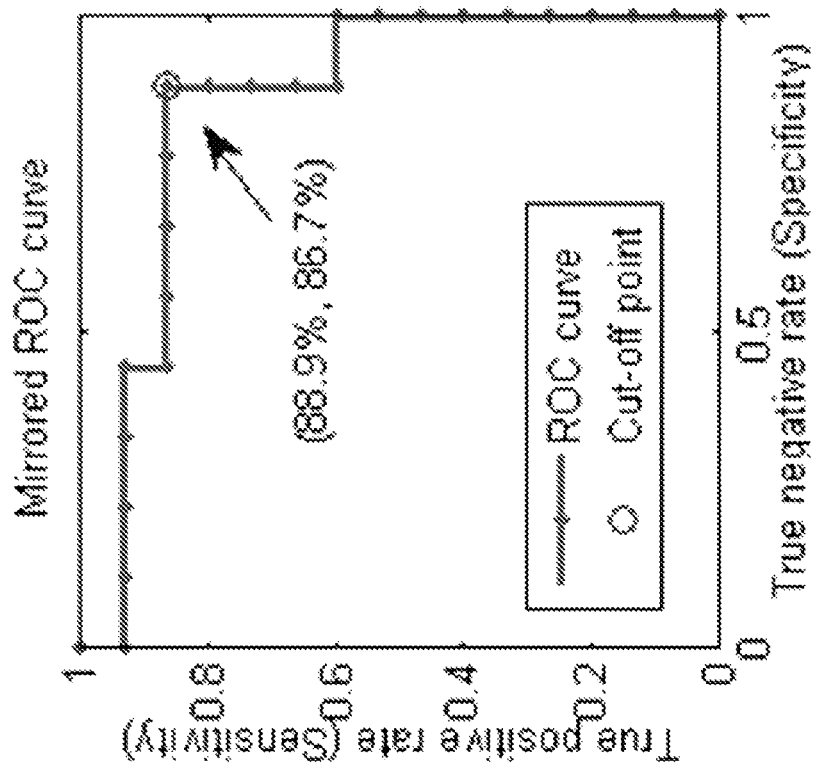
FIG. 6a depicts a graph showing an ROC curve for NPH patient classification against only AD patients in accordance with an illustrative embodiment.

The classification power for the best three one-dimensional and the best three two-dimensional classifiers are indicated in the tables depicted in FIGS. 8 and 9. FIG. 8 depicts a table showing classification power for one-dimensional fitting parameters and binary classifier with group 1: NPH and group 2: AD in accordance with an illustrative embodiment. FIG. 9 depicts a table showing classification power for one-dimensional fitting parameters and binary classifier with group 1: NPH and group 2: AD, PD, DLB in accordance with an illustrative embodiment. Overall, the best differentiation of NPH from the control groups, in both classifier variants, was achieved with the combination of parameters $f_{mix}$ and $\theta$. Estimates on achievable specificity and sensitivity for the best classifier are given by ROC as depicted in FIGS. 6a and 6b. For example, FIG. 6a illustrates the sensitivity and specificity that the method can achieve in differentiating NPH patients from AD, and FIG. 6b illustrates the sensitivity and specificity that the method can achieve in differentiating NPH patients from AD, PD and LBD combined. The ROC points presented in FIGS. 6a and 6b are for the cut-off lines of the form $\theta_{cut} = -0.4 + \beta * f_{mix}$, $\beta \in (1, 3.5)$, with the best cut-off obtained by $\beta = 2.1$.

Three one-dimensional classifiers and three two-dimensional classifiers with the highest Youden's index, for the binary classification with group 1: NPH and group 2: AD are depicted in Table 1 below. The numbers in parentheses represent the nominator and denominator for the given fractional value.

TABLE 1

|  | $f_{CSF}$ | $f_{brain}$ | $\theta$ | ($f_{CSF}$, $\theta$) | ($\sigma_{brain}$, $\theta$) | ($f_{mix}$, $\theta$) |
|---|---|---|---|---|---|---|
| Sensitivity | 0.73 | 1.00 | 0.73 | 0.73 | 0.73 | 0.87 |
|  | (11/15) | (15/15) | (11/15) | (11/15) |  | (13/15) |
| Specificity | 0.56 | 0.33 | 0.78 | 0.89 | 0.92 | 0.89 |
|  | (5/9) | (3/9) | (7/9) | (8/9) |  | (8/9) |
| Y-index | 1.29 | 1.33 | 1.51 | 1.62 | 1.65 | 1.76 |

Three one-dimensional classifiers and three two-dimensional classifiers with the highest Youden's index, for the binary classification with group 1: NPH and group 2: AD, PD, DLB are depicted in Table 2 below. The numbers in parentheses represent nominator and denominator for the given fractional value.

TABLE 2

|  | $f_{brain}$ | $\theta$ | $f_{CSF}$ | (av.MD, $\theta$) | ($f_{brain}$, $\theta$) | ($f_{mix}$, $\theta$) |
|---|---|---|---|---|---|---|
| Sensitivity | 0.87 | 0.73 | 0.87 | 0.80 |  |  |
|  | (13/15) | (11/15) | (13/15) | (12/15) | (13/15) | (13/15) |
| Specificity | 0.52 | 0.80 | 0.68 | 0.84 | 0.88 | 0.96 |
|  | (13/25) | (20/25) | (17/25) | (21/25) | (22/25) | (23/25) |
| Y-index | 1.39 | 1.53 | 1.55 | 1.64 | 1.75 | 1.83 |

As indicate din FIG. 5, the two patients with both NPH and AD appear at the top right corner of the graph. This indicates that these patients have a relatively flat distribution of MD values, coming from a combined effect of cerebral atrophy and high MD within the brain parenchyma.

Other Fitting Parameters

The most conspicuous parameter of the MD histograms, location of the raw data histogram peak, was, on average, at the same position for the NPH patients (mean 8.05e-4 mm$^2$/s, standard deviation (SD) 2.5e-5 mm$^2$/s), AD (mean 8.02e-4 mm$^2$/s, SD 3.0e-5 mm$^2$/s) and PD+DLB (mean 8.08e-4 mm$^2$/s, SD 3.5e-5 mm$^2$/s) and could not yield specificity to distinguish NPH.

As indicated in the table depicted in FIG. 7, parameter $f_{CSF}$ was elevated in NPH and AD compared to PD+DLB patients. This parameter alone yielded relatively good results in differentiating NPH from all the other conditions (sensitivity 87%, specificity 68%), but was not a particularly good indicator of NPH compared to AD (sensitivity 73%, specificity 56%).

Parameter $\mu_{CSF}$ had a mean value of 3.1e-3 mm²/s and SD of 1.6e-4 mm²/s over the entire subject population. This corresponds to the well-known MD value for unrestricted water. There does not appear to be a relationship between the patients' diagnoses and $\mu_{CSF}$ as depicted in the table of FIG. 7.

The misclassified patients were at the extremes of their patient groups' age range, suggesting that age should be considered as a predictor variable. It has been argued recently, in several large studies that effects of aging on MD obey a quadratic law (MD~$\alpha+\beta_1$*age+$\beta_2$*age²), with MD decreasing from birth to approximately 40 years of age and then increasing after age 40. Although the data sample was too small for a rigorous age- and gender-matched analysis, multivariate first order $\theta_{est}=\alpha+\beta_1*f_{mix}+\beta_2$*age and second order $\theta_{est}=\alpha+\beta_1*f_{mix}+\beta_2$*age+$\beta_3$*age² regression analysis was performed to test for possible dependence of $\theta$ on patients' age and $f_{mix}$ as independent predictors. As expected, these models did not achieve the necessary p value (0.05) to justify introduction of age and age² as a predictor variables in the model. With linear regression, the coefficients for the NPH group were $\theta_{NPH}=-0.25+1.37*f_{VD}+0.002$*age and for AD were $\theta_{AD}=-0.68+1.91*f_{mix}+0.006$*age, indicating potentially stronger dependence on age in AD patients.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method to differentiate normal pressure hydrocephalus (NPH) from one or more related brain conditions or disorders comprising:
   generating, by a computing device, a histogram of voxels in an image from a scan of a patient's brain;
   fitting, by the computing device, a curve to the histogram of voxels using a model of brain characteristics, wherein the model comprises at least three functions expressing distribution-groups for voxels and a weighting variable for each of the at least three functions, wherein the at least three functions include a function representing brain tissue, a function representing cerebrospinal fluid (CSF), and a function representing a mix of brain tissue and CSF, and wherein the function representing the mix of brain tissue and CSF enables unequal partial volume voxel distributions of the brain tissue and the CSF;

iteratively changing, by the computing device, the function representing the mix of brain tissue and CSF and a variable within the function representing the mix of brain tissue and CSF that represents a relative amount of brain tissue versus CSF mixed in the voxels such that a best fit of the curve to the histogram is obtained; and comparing, by the computing device, at least the weighting variable for the function representing the mix of brain tissue and CSF to pre-determined values representative of the one or more related brain conditions or disorders.

2. The method of claim 1, further comprising receiving the image from the scan of the patient's brain from a scanning device.

3. The method of claim 1, further comprising scanning, by a scanning device, the patient's brain to produce the image and communicating the image from the scanning device to the computing device.

4. The method of claim 3, wherein the scan comprises a diffusion tensor imaging (DTI) scan of the patient's brain.

5. The method of claim 1, wherein the at least three functions when weighted by respective weighting variables add up to approximate the curve fitting the histogram.

6. The method of claim 1, wherein the comparing comprises plotting the weighting variable for the function representing the mix of brain tissue and CSF and the variable within the function representing the mix of brain tissue and CSF on a graph with one axis representing the weighting variable for the function representing the mix of brain tissue and CSF, and a second axis representing the variable within the function representing the mix of brain tissue and CSF that represents a relative amount of brain tissue versus CSF mixed in the voxels, and wherein the graph has at least one cut-off curve separating normal pressure hydrocephalus (NPH) from the one or more related brain conditions or disorders.

7. The method of claim 6, wherein the one or more related brain conditions or disorders comprise at least one of Alzheimer's disease, Parkinson's disease, and Lewy Body dementia.

8. The method of claim 1, wherein the function representing the mix of brain tissue and CSF comprises a sum of Gaussian distributions representing a homotopy from the function representing CSF to the function representing brain tissue.

9. The method of claim 1, wherein the model is represented by the following equation:

$$P(MD) = f_{brain}P_{brain}(MD) + f_{CSF}P_{CSF}(MD) + f_{mix}P_{VD}(MD)$$

where $$P_{brain}(MD) = \frac{1}{\sqrt{2\pi}\,\sigma_{brain}}\exp\left[\frac{-1}{2}\left(\frac{MD-\mu_{brain}}{\sigma_{brain}}\right)^2\right];$$

$$P_{CSF}(MD) = \frac{1}{\sqrt{2\pi}\,\sigma_{CSF}}\exp\left[\frac{-1}{2}\left(\frac{MD-\mu_{CSF}}{\sigma_{CSF}}\right)^2\right];$$

$$P_{VD}(MD) = \int_0^1 \frac{1}{\sqrt{2\pi}\,\sigma_\theta(t)}\exp\left[\frac{-1}{2}\left(\frac{MD-\mu_\theta(t)}{\sigma_\theta(t)}\right)^2\right]dt;\text{ and}$$

-continued where $\mu_\theta(t) =$ $$t^\theta\mu_{brain} + (1-t^\theta)\mu_{CSF} \text{ and } \sigma_\theta(t) = \sqrt{t^{2\theta}\sigma_{brain}^2 + (1-t^\theta)^2\sigma_{CSF}^2}\,,$$

wherein $P_{brain}(MD)$ corresponds to a brain Gaussian function, $P_{CSF}(MD)$ corresponds to a CSF Gaussian function, $P_{VD}(MD)$ corresponds to a Generalized Voss-Dyke function, $\mu_\theta(t)$ corresponds to a homotopy map, $\sigma_\theta(t)$ corresponds to a standard deviation function, MD corresponds to mean diffusivity histogram values, t corresponds to an integration variable, $f_{brain}$ corresponds to histogram fractions of brain parenchyma, $f_{CSF}$ corresponds to histogram fractions of CSF, $f_{mix}$ corresponds to histogram fractions of mixed voxels, $\mu_{CSF}$ corresponds to a mean of the CSF Gaussian, $\mu_{brain}$ corresponds to a mean of the brain Gaussian, $\sigma_{brain}$ corresponds to a standard deviation of the brain Gaussian, $\sigma_{CSF}$ corresponds to a standard deviation of the CSF Gaussian, and $\theta$ corresponds to a slope of a Generalized Voss-Dyke function.

10. The method of claim 8, wherein the function representing the mix of brain tissue and CSF is represented by the following equation:

$$P_{VD}(MD) = \int_0^1 \frac{1}{\sqrt{2\pi}\,\sigma_\theta(t)}\exp\left[\frac{-1}{2}\left(\frac{MD-\mu_\theta(t)}{\sigma_\theta(t)}\right)^2\right]dt,$$

$P_{VD}(MD)$ corresponds to a Generalized Voss-Dyke function, $\mu_\theta(t)$ corresponds to a homotopy map, $\sigma_\theta(t)$ corresponds to a standard deviation function, MD corresponds to mean diffusivity histogram values, t corresponds an integration variable.

11. The method of claim 10, wherein small values of $\theta$ indicate a higher percentage of voxels with mean diffusivity (MD) values closer to that of the brain than CSF, and wherein $\theta$ corresponds to a slope of a Generalized Voss-Dyke function.

12. The method of claim 1, wherein the generating the histogram of voxels comprises generating mean diffusivity (MD) values from the image and placing the MD values in bins of the histogram.

13. The method of claim 1, wherein the function representing the mix of brain tissue and CSF enables unequal partial volume voxel distributions of the brain tissue and the CSF such that a ratio of the brain tissue to the CSF is not necessarily equal.

14. A non-transitory computer-readable medium having instructions, executable by a computer, for causing the computer to perform operations to differentiate normal pressure hydrocephalus (NPH) from one or more related brain conditions or disorders, the operations comprising:

generating a histogram of voxels in an image from a scan of a patient's brain;

fitting a curve to the histogram of voxels using a model of brain characteristics, wherein the model comprises at least three functions expressing distribution-groups for voxels and a weighting variable for each of the at least three functions, wherein the at least three functions include a function representing brain tissue, a function representing cerebrospinal fluid (CSF), and a function representing a mix of brain tissue and CSF, and wherein the function representing the mix of brain tissue and CSF enables unequal partial volume voxel distributions of the brain tissue and the CSF;

iteratively changing the function representing the mix of brain tissue and CSF and a variable within the function representing the mix of brain tissue and CSF that represents a relative amount of brain tissue versus CSF mixed in the voxels such that a best fit of the curve to the histogram is obtained; and comparing the weighting variable for the function representing the mix of brain tissue and CSF to pre-determined values representative of the one or more related brain conditions or disorders.

15. The non-transitory computer-readable medium of claim 14, wherein the functions when weighted by respective weighting variables add up to approximate the curve fitting the histogram.

16. The non-transitory computer-readable medium of claim 14, wherein the comparing comprises plotting the weighting variable for the function representing the mix of brain tissue and CSF and the variable within the function representing the mix of brain tissue and CSF on a graph with one axis representing the weighting variable for the function representing the mix of brain tissue and CSF, and a second axis representing the variable within the function representing the mix of brain tissue and CSF that represents a relative amount of brain tissue versus CSF mixed in the voxels, and wherein the graph has at least one cut-off curve separating normal pressure hydrocephalus (NPH) from the one or more related brain conditions or disorders.

17. The non-transitory computer-readable medium of claim 14, wherein the function representing the mix of brain tissue and CSF comprises a sum of Gaussian distributions representing a homotopy from the function representing CSF to the function representing brain tissue.

18. The non-transitory computer-readable medium of claim 14, wherein the function representing the mix of brain tissue and CSF is represented by the following equation:

$$P_{VD}(MD) = \int_0^1 \frac{1}{\sqrt{2\pi}\, \sigma_\theta(t)} \exp\left[\frac{-1}{2}\left(\frac{MD - \mu_\theta(t)}{\sigma_\theta(t)}\right)^2\right] dt,$$

wherein $P_{brain}(MD)$ corresponds to a brain Gaussian function, $P_{CSF}(MD)$ corresponds to a CSF Gaussian function, $P_{VD}(MD)$ corresponds to a Generalized Voss-Dyke function, $\mu_\theta(t)$ corresponds to a homotopy map, $\sigma_\theta(t)$ corresponds to a standard deviation function, MD corresponds to mean diffusivity histogram values, t corresponds to an integration variable.

19. A system to differentiate normal pressure hydrocephalus (NPH) from one or more related brain conditions or disorders, the system comprising:

a scanning device configured to scan a patient's brain to produce an image of the patient's brain; and a disorder differentiation device configured to:
  receive the image of the patient's brain from the scanning device;
  generate a histogram of voxels in the image;
  fit a curve to the histogram of voxels using a model of brain characteristics, wherein the model comprises at least three functions expressing distribution-groups for voxels and a weighting variable for each of the at least three functions, wherein the at least three functions include a function representing brain tissue, a function representing cerebrospinal fluid (CSF), and a function representing a mix of brain tissue and CSF, and wherein the function representing the mix of brain tissue and CSF enables unequal partial volume voxel distributions of the brain tissue and the CSF;
  iteratively change the function representing the mix of brain tissue and CSF and a variable within the function representing the mix of brain tissue and CSF that represents a relative amount of brain tissue versus CSF mixed in the voxels such that a best fit of the curve to the histogram is obtained; and
  compare the weighting variable for the function representing the mix of brain tissue and CSF to pre-determined values representative of the one or more related brain conditions or disorders.

20. The system of claim 19, further comprising a database of collected normal and diseased-patient data, and wherein the disorder differentiation device is configured to compare the weighting variable for the function representing the mix of brain tissue to the collected normal and diseased-patient data from the database.

21. A method to weight partial voxels in an image of at least two substances and differentiate from one or more known mixes thereof, the method comprising:

generating, by a computing device, a histogram of voxels in an image of the at least two substances, wherein the at least two substances comprise a first substance intermixed with a second substance;

fitting, by the computing device, a curve to the histogram of voxels using a model, wherein the model comprises at least three functions expressing distribution-groups for voxels and a weighting variable for each of the at least three functions, wherein the at least three functions include a function representing the first substance, a function representing the second substance, and a function representing a mix of the first and second substances, and wherein the function representing the mix of the first and second substances enables unequal partial volume voxel distributions of the first and second substances;

iteratively changing, by the computing device, a plurality of parameters of the model and a variable within the function representing the mix of the first and second substances that represents a relative amount of first substance to second substance mixed in the voxels such that a best fit to the curve is obtained; and comparing, by the computing device, the weighting variable for the function representing the mix of the first and second substances to pre-determined values representative of the one or more known mixes.

22. The method of claim 21, wherein the plurality of parameters comprises two or more of $f_{brain}$, $f_{CSF}$, $f_{mix}$, $\mu_{brain}$, $\mu_{CSF}$, $\sigma_{brain}$, $\sigma_{CSF}$ and $\theta$, wherein $f_{brain}$ corresponds to histogram fractions of brain parenchyma, $f_{CSF}$ corresponds to histogram fractions of CSF, $f_{mix}$ corresponds to histogram fractions of mixed voxels, $\mu_{CSF}$ corresponds to a mean of a CSF Gaussian, $\mu_{brain}$ corresponds to a mean of the brain Gaussian, $\sigma_{brain}$ corresponds to a standard deviation of a brain Gaussian, $\sigma_{CSF}$ corresponds to a standard deviation of the CSF Gaussian, and $\theta$ corresponds to a slope of a Generalized Voss-Dyke function.

* * * * *